United States Patent [19]

Batchelor et al.

[11] Patent Number: 4,902,701

[45] Date of Patent: Feb. 20, 1990

[54] TETRAZOLYL SUBSTITUTED TRICYCLIC COMPOUNDS AND PHARMACOLOGICAL COMPOSITIONS THEREOF

[75] Inventors: John F. Batchelor, Beckenham; Richard M. Hyde, Croydon; Williasm R. King, Bickley; David J. Livingstone, Beckenham, all of England

[73] Assignee: Burroughs Welcome Co., Research Triangle Park, N.C.

[21] Appl. No.: 903,834

[22] Filed: Sep. 3, 1986

Related U.S. Application Data

[62] Division of Ser. No. 782,620, Oct. 2, 1985, abandoned, which is a division of Ser. No. 488,051, Jan. 25, 1983, abandoned.

[30] Foreign Application Priority Data

Apr. 27, 1982 [GB] United Kingdom ................ 8212139
Oct. 21, 1982 [GB] United Kingdom ................ 8230055

[51] Int. Cl.$^4$ .................... C07D 407/02; A61K 31/41
[52] U.S. Cl. .................................... 514/381; 548/252; 548/253
[58] Field of Search ................ 548/252, 253; 514/381

[56] References Cited

U.S. PATENT DOCUMENTS 3,706,768  12/1972  Bays ................................. 548/252
4,061,768  12/1977  Gorvin .............................. 549/393

Primary Examiner—David B. Springer
Attorney, Agent, or Firm—Donald Brown

[57] ABSTRACT

Tricyclic compounds of formula (I)

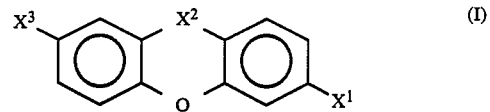

wherein
  $X^1$ is a carboxyl or 5-tetrazolyl group
  $X^2$ is carbonyl or methylene
  $X^3$ is hydroxyl or a group $-X^4(C_nH_{2n})X^5$
where
  $X^4$ is oxygen or sulphur
  $X^5$ is hydrogen or a group $-OX^6$
where
  $X^6$ is hydrogen, alkanoyl of 1 to 4 carbon atoms or a group $-(C_mH_{2m})X^7$
where
  $X^7$ is hydrogen or a group $-OX^8$
where
  $X^8$ is hydrogen or alkanoyl of 1 to 4 carbon atoms and m and n are each, independently, an integer from 1 to 4, together with salts thereof,
  provided that when $X^5$ is a group $-OX^6$ then n is always greater than 1 and $X^4$ and $X^5$ are attached to different carbon atoms
  and that when $X^7$ is a group $-OX^8$ then m is always greater than 1 and no single carbon atom in the radical $-(C_mH_{2m})-$ is attached to two oxygen atoms.

These compounds are of value in medicine in circumstances where it is desirable to provide a more effective delivery of oxygen to the tissues; in vivo applications include the relief or amelioration of tissue hypoxia as in, for example, cardiac or cerebral ischaemia while in vitro they maintain the oxygen-delivery capacity of stored red blood cells and prolong the cells' useful storage life.

The invention is also directed to methods for the preparation of the compounds, to pharmaceutical formulations and other presentation forms containing them and the preparation thereof, to the use of the compound in medicine, and to novel intermediates for the said compounds and the preparation thereof.

28 Claims, No Drawings

TETRAZOLYL SUBSTITUTED TRICYCLIC COMPOUNDS AND PHARMACOLOGICAL COMPOSITIONS THEREOF

This application is a division of application Ser. No. 782,620 filed Oct. 2, 1985, now abandoned, which is a division of application Ser. No. 488,051, filed Jan. 25, 1983, also abandoned.

This invention relates to tricyclic compounds useful in medicine, to the preparation of such compounds, to pharmaceutical formulations and other presentation forms containing such compounds and the preparation thereof, to the use of the compounds in medicine, and to novel intermediates for the said compounds and the preparation thereof.

The present invention more particularly relates to the novel tricyclic compounds of formula (I),

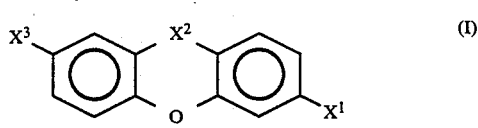

as hereinafter defined, which are of value in both human and veterinary medicine in enabling an increase in oxygen liberation from oxyhaemoglobin.

Human Haemoglobins are composed of four polypeptide (globin) chains which together comprise the haemoglobin tetramer; each chain surrounds a porphyrin molecule (haem) containing a central iron atom to which oxygen is reversibly bound. When a graph is plotted of the percentage saturation of haemoglobin with oxygen (ordinate) against the partial pressure of oxygen, sometimes called the oxygen tension (abscissa) a characteristic sigmoid curve is obtained, the oxygen-dissociation curve. A displacement of the curve to the left of the "normal" position would indicate an increase in the affinity for oxygen of the haemoglobin, a lower oxygen tension then being required to produce a given percentage saturation, while conversely a displacement to the right would indicate a reduced oxygen affinity and hence a requirement for a higher oxygen tension for a given percentage saturation. It follows that upon displacement of the curve to the right there is a reduction in the percentage of oxyhaemoglobin present at any given oxygen tension and hence an increased liberation of oxygen upon a fall in tension to any given level.

The compounds of formula (I), as hereinafter defined, induce an in vitro right-displacement of the oxygen-dissociation curve (a) of fresh whole human blood, and (b) of whole human blood subjected to a procedure (incubation overnight at 37° C.) producing changes similar to those seen in blood stored for extended periods by transfusion services and the like (vide infra).

The compounds thus have applications both in vivo and in vitro in circumstances where it is desirable to provide a more effective delivery of oxygen to the tissues of the (eventual) recipient.

In vivo applications for the compounds include the following, many of which may be together classed as the relief or amelioration of conditions wherein the delivery of oxygen to the tissues is impaired, i.e. wherein there is tissue hypoxia:

the treatment of shock the treatment of cardiac ischaemia, for example after myocardial infarction (coronary thrombosis), and the relief of sequelae thereto such as angina pectoris the treatment of cerebral ischaemia and of cerebrovascular accidents in general the relief of intermittent claudication the treatment of placental insufficiency in gravid females the treatment of certain anaemic conditions and in particular pathological anaemia in preterm infants the treatment of the microvascular complications of diabetes mellitus the treatment of hypovolaemic anaemia of trauma (the so-called "missing blood syndrome")

as an adjunct to anaesthesia in cardiac bypass surgery, in particular in patients having compromised respiration applications in which a pathological tissue or invading organism is made more sensitive to treatment by increasing the partial pressure of oxygen in its environment, for example: the radiosensitization of tumours as an adjunct to deep X-ray therapy, with or without concomitant hyperbaric oxygen treatment the treatment of infections of oxygen-sensitive parasites, for example, anaerobic bacteria.

A major in vitro application for the compounds is in the field of blood storage. As is well known there is an ever-present need for human blood by medical services throughout the world for use in a wide variety of life-supportive measures. For the majority of recipients whole blood is the only acceptable material as although a number of alternatives have been proposed, none has been found to be a completely satisfactory substitute. The collection, storage and distribution of blood is generally catered for by specialist transfusion services or "blood banks" as exemplified by the National Blood Transfusion Service in the United Kingdom. The effective and economic operation of such agencies is however in large measure governed by the fact that whole blood or, more correctly, the red blood cells (erythrocytes) therein, even when stored as customarily at 4° C., have a very limited "shelf-life" generally accepted as 21 days after removal from the donor. By the end of this period they are considered unsuitable for transfusion and are discarded and there has been considerable research into methods for prolonging the useful life of stored red blood cells and thus reducing the wastage due to "out-dating".

A particular feature of the ageing of red blood cells during storage is a progressive left-displacement of the oxygen-dissociation curve associated with a fall in intracellular levels of 2,3-diphosphoglycerate (DPG), the erythrocytes' natural right-displacement effector. As previously indicated a left-displacement is associated with the haemoglobin having an increased affinity for oxygen and hence ageing cells exhibit a progressive decline in their ability to deliver oxygen to the peripheral tissues following transfusion. Although this property is gradually restored within the recipient's body as DPG levels recover, the initial deficiency is of literally vital significance as the prime reason for transfusing red blood cells (as distinct from just plasma) is generally the immediate prevention or reversal of tissue hypoxia (vide supra). The present compounds, in displacing the oxygen-dissociation curve to the right, are of value not only in maintaining the oxygen-delivery capacity of stored red blood cells, thus improving their quality and providing improved oxygen-delivery in the immediate post-transfusion period, but also in prolonging their useful storage life.

In formula (I), as set forth above, $X^1$ is a carboxyl or 5-tetrazolyl group $X^2$ is carbonyl or methylene $X^3$ is hydroxyl or a group —$X^4(C_nH_{2n})X^5$ where $X^4$ is oxygen or sulphur $X^5$ is hydrogen or a group —$OX^6$ where $X^6$ is hydrogen, alkanoyl of 1 to 4 carbon atoms or a group —$(C_mH_{2m})X^7$ where $X^7$ is hydrogen or a group —$OX^8$ where $X^8$ is hydrogen or alkanoyl of 1 to 4 carbon atoms and m and n are each, independently, an integer from 1 to 4, together with salts thereof, provided that when $X^5$ is a group —$OX^6$ then n is always greater than 1 and $X^4$ and $X^5$ are attached to different carbon atoms and that when $X^7$ is a group —$OX^8$ then m is always greater than 1 and no single carbon atom in the radical —$(C_mH_{2m})$— is attached to two oxygen atoms.

As herein understood, the 5-tetrazolyl group is that having the structural formula

which thus embraces both tautomeric forms thereof respectively identifiable as 5-/1H/-tetrazolyl and 5-/2H/-tetrazolyl.

When m and/or n is 3 or 4 the moieties —$(C_mH_{2m})$— and —$(C_nH_{2n})$— can be linear or branched.

In the salts of the compounds of formula (I) the biological activity resides in the tricyclic (anion) moiety and the identity of the cation is of less importance although for use in medicine it is preferably pharmacologically acceptable to the eventual recipient. Suitable salts include ammonium salts, alkali metal salts such as sodium and potassium salts, alkaline earth salts such as magnesium and calcium salts, and salts formed with organic bases, for example, amine salts derived from mono-, di- or tri(lower alkyl) or (lower alkanol)amines such as triethanolamine and diethylaminoethylamine, and salts with heterocyclic amines such as piperidine, pyridine, piperazine and morpholine.

As a class of compounds within formula (I) may be mentioned those wherein:

$X^1$ is a carboxyl or 5-tetrazolyl group $X^2$ is carbonyl or methylene $X^3$ is hydroxyl or a group —$X^4(C_nH_{2n})X^5$ where $X^4$ is oxygen or sulphur $X^5$ is hydrogen or a group —$OX^6$ where $X^6$ is hydrogen or alkanoyl of 1 to 4 carbon atoms and n is an integer from 1 to 4, together with salts thereof, provided that when $X^5$ is a group —$OX^6$ then n is always greater than 1 and $X^4$ and $X^5$ are attached to different carbon atoms.

As subclasses of compounds written formula (I) may be mentioned those wherein:

(i) $X^1$ is 5-tetrazolyl and salts thereof (ii) $X^2$ is carbonyl (iii) $X^3$ is a group —$X^4(C_nH_{2n})X^5$ (iv) $X^4$ is oxygen (v) $X^5$ is hydrogen (vi) $X^5$ is a group —$OX^6$ where $X^6$ is hydrogen, i.e. $X^5$ is hydroxyl (vii) n is 2 or 3.

Two further classes of compounds within formula (I) respectively comprise those wherein (a) $X^1$ is 5-tetrazolyl, $X^2$ is carbonyl and $X^3$ is —$O(C_nH_{2n})H$; and (b) $X^1$, $X^2$ and $X^3$ are as hereinbefore defined, provided that $X^3$ is other than —$O(C_nH_{2n})H$ when $X^1$ and $X^2$ are respectively 5-tetrazolyl and carbonyl; together with salts thereof.

Preferred compounds within formula (I) are

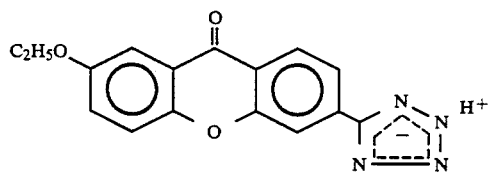

chemically named 2-ethoxy-6-(5-tetrazolyl)xanthone, together with salts thereof, and in particular

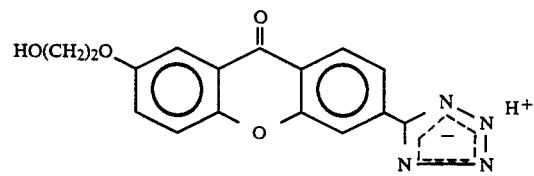

chemically named 2-(2-hydroxyethoxy)-6-(5-tetrazolyl)xanthone, together with salts thereof.

Where the compounds of formula (I), as above defined, include an asymmetric centre the said formula should be understood to include all optical isomers embraced thereby and mixtures thereof.

The compounds of formula (I) and their salts may be prepared by those methods known in the art for the synthesis of compounds of analogous structure and in this regard reference is made, by way of illustration only, to the following standard texts:

(i) *"Protective Groups in Organic Chemistry"* ed. J. F. W. McOmie, Plenum Press (1973), ISBN 0-306-30717-0;

(ii) *"Compendium of Organic Synthetic Methods"* ed. I. T. Harrison and S. Harrison, Wiley-Interscience, Vol. I (1971) ISBN 0-471-35550-X, Vol. II (1974) ISBN 0-471-35551-8 and Vol. III (ed. L. S. Hegedus and L. Wade) (1977) ISBN 0-471-36752-4; and (iii) Rodd's *"Chemistry of Carbon Compounds"* second edition, Elsevier Publishing Company.

All references identified hereinabove or in the following are hereby incorporated herein by reference thereto.

(1) One method, applicable to both the xanthenes ($X^2$ is methylene) and the xanthones ($X^2$ is carbonyl) within formula (I), comprises cyclization in the presence of a base of a compound of formula (II)

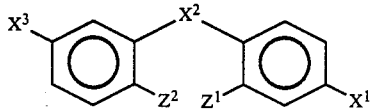

wherein $X^1$, $X^2$ and $X^3$ are as defined in formula (I) and one of $Z^1$ and $Z^2$ is hydroxyl or an ester thereof and the other is a leaving atom or group.

Amongst suitable leaving atoms/groups are halo (for example chloro), nitro and sulphinyl while appropriate bases include alkali metal alkoxides such as sodium methoxide and sodium ethoxide.

(2) The xanthones may also be prepared by cyclization in the presence of a Lewis or protonic acid of a compound of formula (III)

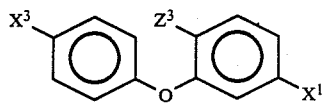

wherein $X^1$ and $X^3$ are as defined in formula (I) and $Z^3$ is a carboxyl group, a derivative thereof or a formyl group.

Suitable identities for $Z^3$ as carbonyl group derivatives include cyano, carbamyl and chlorocarbonyl. Suitable Lewis acids include aluminium trichloride, ferric chloride, phosphorous oxychloride and boron trifluoride while preferred protonic acids are polyphosphoric (tetraphosphoric) and sulphuric acids. The reaction is preferably effected at a temperature in the range 20° to 160° C.

(3) A further preparation of the xanthones comprises selective oxidation of the corresponding xanthene also within formula (I).

A suitable selective oxidising agent comprises oxygen in the presence of Triton B (tetramethylammonium hydroxide) and pyridine.

(4) Conversely, the xanthenes may be prepared by selective reduction of the corresponding xanthone within formula (I).

Suitable selective reducing agents include zinc and an acid, for example acetic or hydrochloric acid, and zinc amalgam and concentrated hydrochloric acid (the Clemmensen reduction).

(5) The compounds of formula (I) wherein $X^1$ is 5-tetrazolyl may be prepared by the reaction with hydrazoic acid or a salt thereof or with nitrous acid, as appropriate, of a compound of formula (IV)

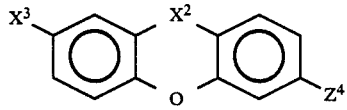

wherein $X^2$ and $X^3$ are as defined in formula (I) and $Z^4$ is a 5-tetrazolyl group precursor as herein defined.

When hydrazoic acid or a salt thereof is employed the 5-tetrazolyl group precursor is a group of formula

wherein $Z^5$ and $Z^6$ together form a bond (nitrile), $Z^5$ is hydrogen or alkyl of 1 to 4 carbon atoms and $Z^6$ is alkoxy of 1 to 6 carbon atoms (imidoester), alkylthio of 1 to 6 carbon atoms (imidothioester), hydrazino (amidrazone), or amino (amidine) or $Z^5$ is hydroxyl and $Z^6$ is amino (amidoxime). The reaction is desirably effected in a polar aprotic liquid medium, for example dimethylsulphoxide, dimethylformamide, hexamethylphosphoramide, dimethylacetamide, N-methyl-2-pyrrolidone, sulpholane and acetonitrile and mixtures thereof, and preferably with a hydrazoic acid salt such as sodium or ammonium azide.

When nitrous acid is employed the 5-tetrazolyl group precursor is also a group of formula

wherein $Z^5$ is hydrogen or alkyl of 1 to 4 carbon atoms and $Z^6$ is hydrazino (amidrazone), or $Z^5$ is hydrogen and $Z^6$ is amino (amidine). In the latter case selective reduction of the initially formed nitrosation product, with or without prior isolation and using an agent such as sodium amalgam, is required to provide the 5-tetrazolyl end product.

(6) The compounds of formula (I) wherein $X^1$ is carboxyl may be prepared by hydrolysis of a compound of formula (V)

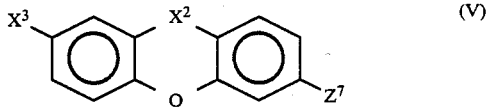

wherein $X^2$ and $X^3$ are as defined in formula (I) and $Z^7$ is a carboxyl group precursor as herein defined.

Suitable identities for $Z^7$ include cyano, trichloromethyl and a group —$COZ^8$ where $Z^8$ is a leaving, preferably nucleophilic atom or group such as halo, trichloromethyl, alkoxy of 1 to 6 carbon atoms and optionally-substituted amino.

The hydrolysis may be effected by heating with either a dilute aqueous mineral acid, for example sulphuric or hydrochloric acid, optionally in the presence of an organic acid such as acetic acid, or with a base such as an alkali metal hydroxide or alkoxide, for example aqueous sodium or potassium hydroxide, sodium methoxide and sodium ethoxide.

It will be appreciated that the basic conditions appropriate to cyclization of a compound of formula (II) (vide (1) supra) will also effect hydrolysis of a group $Z^7$ as defined in formula (V) and that the former synthetic approach may hence be extended to include, where necessary, a combined ("one-pot") cyclization/hydrolysis procedure. The starting material for method (1) may thus more generally be represented by formula (IIa)

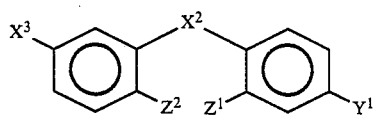

wherein $X^2$ and $X^3$ are as defined in formula (I), one of $Z^1$ and $Z^2$ is hydroxyl or an ester thereof and the other is a leaving atom or group and $Y^1$ is a group $X^1$ as defined in formula (I) or a carboxyl group precursor as herein defined.

(7) The carboxyl compounds of formula (I) may also be prepared by selective oxidation of a compound of formula (VI)

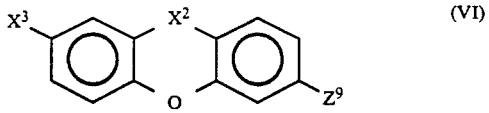

wherein $X^2$ and $X^3$ are as defined in formula (I) and $Z^9$ is alkyl or alkanoyl of 1 to 6 carbon atoms.

Alkyl identities for $Z^9$ may be oxidised with agents such as acid or alkaline aqueous potassium permanganate, an aqueous dichromate salt such as sodium or potassium dichromate in the presence of acetic acid, oxygen in the presence of a catalyst such as a cobalt, manganese or vanadium salt or oxide and chromium trioxide with for example acetic or sulphuric acid while oxidation of an alkanoyl group may be effected by means of an agent such as nitric acid, an aqueous dichromate salt such as sodium or potassium dichromate in the presence of acetic acid, an aqueous salt of hypobromous or hypochlorous acid in the presence of a base and chromium trioxide with for example acetic or sulphuric acid.

It will be appreciated that the formation in this manner of the carboxyl identity for $X^1$ may, if desired, be effected in association with the conversion of a xanthene precursor to a xanthone end-product (vide (3) supra), the two procedures being conducted either sequentially or simultaneously (as a "one-pot" reaction) depending upon the identity of the selective oxidising agent(s) employed. The starting material for the oxidative preparation of the compounds of formula (I) may thus generally be represented by formula (VII)

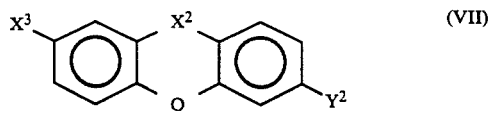

wherein $X^2$ and $X^3$ are as defined in formula (I) and $Y^2$ is a group $X^1$ as defined in formula (I) or alkyl or alkanoyl of 1 to 6 carbon atoms, provided that when $X^2$ is carbonyl then $Y^2$ is always alkyl or alkanoyl.

(8) The carboxyl xanthenes of formula (I), i.e. where $X^1$ is carboxyl and $X^2$ is methylene, may be prepared by carboxylation of a compound of formula (VIII)

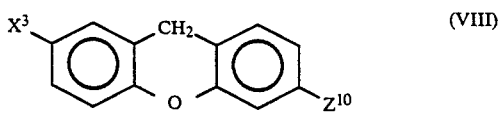

wherein $X^3$ is as defined in formula (I) and $Z^{10}$ is halo, preferably bromo or iodo.

This may be effected by for example reacting the compound (VIII) in ethereal solution with either lithium or magnesium, in the latter case to yield the appropriate Grignard reagent, and then contacting the mixture with gaseous or solid carbon dioxide.

(9) A further synthetic approach comprises conversion of a compound of formula (IX)

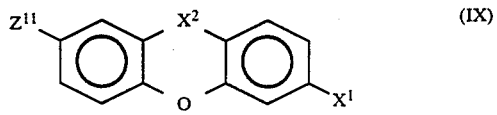

wherein $X^1$ and $X^2$ are as defined in formula (I) and $Z^{11}$ is a group convertible to a group $X^3$ also as defined in formula (I).

Compounds wherein $X^3$ is hydroxyl may be prepared by hydrolysis of a suitable precursor, for example by reaction with water of a corresponding diazonium salt ($Z^{11}$ is $-N_2^+W^-$ where $W^-$ is an anion such as chloride, bromide and hydrogen sulphate), the latter being prepared by the action of nitrous acid on the amine ($Z^{11}$ is amino). The diazonium salts may also be converted to the corresponding alkylthio end-products (wherein $X^4$ is sulphur and $X^5$ is hydrogen) by reaction with an appropriate potassium alkyl xanthate and sequential decomposition of the successively formed diazoxanthate and aromatic xanthate by warming in a faintly acidic cuprous medium (the Leuckart synthesis). The alkylthio compounds may also be prepared by alkylation of the corresponding thiol ($Z^{11}$ is mercapto) which may be obtained by for example alkaline hydrolysis of the previously mentioned aromatic xanthates.

The hydroxyl compounds may also be prepared from precursors having as $Z^{11}$ a group $-OZ^{12}$ which is convertible to hydroxyl. Suitable identities for the moiety $Z^{12}$ include alkyl, for example alkyl of 1 to 4 carbon atoms and in particular methyl, ethyl, isopropyl and t-butyl; aralkyl such as benzyl; acyl such as alkanoyl, in particular alkanoyl of 1 to 6 carbon atoms, for example acetyl; and tetrahydropyranyl. Such groups may be removed, i.e. replaced by hydrogen, by methods standard in the art. Thus removal of an alkyl group may be effected using for example magnesium iodide or sodium thiocresolate, by heating with aluminium trichloride in xylene or (at reduced temperatures) by use of an agent such as boron trichloride or tribromide in a medium such as dichloromethane; an acyl group may be removed by base hydrolysis; an alkyl group and tetrahydropyranyl may be removed by acid hydrolysis, for example using hydrogen bromide in acetic acid; and hydrogenolysis (for example using a palladium charcoal catalyst) may be used to remove an aralkyl group.

It will be appreciated that certain of the above-described conditions for removal of an alkyl group will also be suitable for effecting cyclization as described in (2) supra and that hence the hydroxyl xanthones of formula (I) may be prepared by a "one pot" cyclization/dealkylation of the alkoxy compounds of formula (III) (wherein $X^4$ is oxygen and $X^5$ is hydrogen).

Alkoxy compounds may be prepared by alkylation of the corresponding hydroxyl compound, for example by use of an alkyl halide or dialkyl sulphate and an alkali such as an alkali metal hydride or carbonate.

The hydroxyl compounds may be converted to the corresponding hydroxyalkoxy compounds (wherein $X^4$ is oxygen and $X^5$ is hydroxyl) by for example reaction with the appropriate alkylene oxide or carbonate and the hydroxyalkylthio compounds (wherein $X^4$ is sulphur and $X^5$ is hydroxyl) may be similarly prepared from the corresponding thiol ($Z^{11}$ is mercapto); when in the said starting materials $X^1$ is carboxyl the latter group may be simultaneously esterified by this procedure, the desired end-product then being obtained by selective hydrolysis thereof (vide (6) supra). The end-products wherein $X^5$ is alkanoyloxy (i.e. $X^6$ is alkanoyl) may be prepared from the corresponding hydroxyalkoxy or hydroxyalkylthio compounds, as appropriate, by conventional alkanoylation procedures and the latter may be obtained by hydrolysis of the former.

In the preparation of the compounds of formula (I) by the above-described methods it will be understood that where the groups $X^1$ and $X^3$ are formed prior to the complete formation of the desired end-product it may in some instances be desirable to protect said group(s) from reaction in the final synthetic step(s), and subsequently regenerate them by appropriate deprotection procedures, using techniques well known in the art; alternatively the formation of $X^1/X^3$ may advantageously comprise the final step in the synthetic sequence.

The compounds of formula (I) may be isolated as the acids or as salts thereof and it will be appreciated that the said acids may be converted to salts thereof, and the reverse, and the salts converted to salts formed with other cations, by techniques well-known and conventional in the art. Thus, those salts which are not themselves pharmacologically acceptable are of value in the preparation of the parent carboxyl or 5-tetrazolyl acids and of pharmacologically acceptable salts thereof.

When the preparative procedures herein described provide a mixture of optical or other isomers of a compound of formula (I) or of an intermediate thereto, the individual isomers may be separated by appropriate conventional techniques.

The compounds the formula (I), as above defined, may be used in both human and veterinary medicine in circumstances such as those previously identified where it is desirable to provide a more effective delivery of oxygen to the tissues of the (eventual) recipient. When administered in vivo the compounds may be used both on a regular maintenance basis and for the relief or amelioration of acute crisis states.

For in vivo use the compounds may be administered to the human or non-human recipient by a route selected from oral, parenteral (including subcutaneous, intradermal, intramuscular and intravenous) and rectal. The size of an effective dose of a compound will depend upon a number of factors including the identity of the recipient, the precise condition to be treated and its severity and the route of administration and will ultimately be at the discretion of the attendant physician or veterinarian. An effective dose will generally be in the range 1 to 500 mg/kg bodyweight of recipient per day, more generally in the range 10 to 250 mg/kg bodyweight per day and most often in the range 25 to 100 mg/kg bodyweight per day, a particularly suitable dose being 50 mg/kg bodyweight per day (all doses calculated as the carboxyl or 5-tetrazolyl acid of formula (I); for salts the figures would be adjusted proportionately). The desired dose is preferably presented as between two and four sub-doses administered at appropriate intervals throughout the day. Thus where two sub-doses are employed each will generally be in the range 0.5 to 250, more generally 5 to 125 and most often 12.5 to 50 mg (acid)/kg bodyweight with an optimum of 25 mg(acid/kg bodyweight.

A daily dose for a human being weighing of the order of 50 kg will thus generally be in the range 50 mg to 25 g (acid), more generally in the range 500 mg to 12.5 g (acid) and most often in the range 1.25 g to 5 g (acid) and may be conveniently presented as two equal unit sub-doses of 25 mg to 12.5 g (acid), more generally 250 mg to 6.25 g (acid) and most often 0.625 g to 2.5 g (acid). Optimally a human daily dose is 2.5 g (acid) conveniently presented as two unit sub-doses each of 1.25 g (acid). For veterinary use, for example in the treatment of non-human mammals such as cats, dogs, cattle sheep, pigs and horses, the above-recited doses would be increased or decreased at the discretion of the veterinarian having regard to the weight and identity of the recipient.

While it is possible for the compounds of formula (I) to be administered as the raw chemical it is preferable to present them as a pharmaceutical formulation preparation. The formulations of the present invention, for human or for veterinary use, comprise a compound of formula (I), as above defined, together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous) and rectal administration although the most suitable route may depend upon for example the condition and identity of the recipient. The formulations may conveniently be presented in unit dosage form and may be prepared by any of the methods well known in the art of pharmacy. All methods include the step of bringing into association the compound of formula (I) (the active ingredient) with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter and polyethylene glycol.

Preferred unit dosage formulations are those containing a daily dose or unit daily sub-dose, as hereinabove recited, or an appropriate fraction thereof, of a compound of formula (I).

It should be understood that in addition to the ingredients particularly mentioned above the formulations of this invention may include other agents conventional in the art having regard to the type of formulation in question, for example those suitable for oral administration may include flavouring agents.

The compounds of formula (I) may also be presented as depot formulations of the kind known in the art from which the active ingredient is released, over a prolonged period, once the formulation is in place within the body of the recipient.

A further application for the compounds of formula (I) is the extracorporeal treatment of blood from the (generally human) patient. As one possibility such treatment may be conducted in a batch-wise manner by removing an appropriate volume of blood, admixing it with the compound and transfusing the treated blood back into the patient. As an alternative possibility the treatment may be on a continuous basis, analogous to the well-known techniques for haemodialysis, whereby for a period of time blood is continuously withdrawn, admixed with the compound and passed back into the patient. Both procedures should be conducted under sterile conditions and may be repeated as often as necessary. An effective blood concentration of a compound of formula (I) will generally be in the range 0.1 mM to 50 mM, more generally in the range 0.5 mM to 25 mM and most often in the range 1 mM to 10 mM, with an optimum concentration of 3 mM.

For in vitro use in the storage of red blood cells as previously described the compounds are conveniently admixed with the cells in the vessel in which the latter are collected and stored; this conventionally takes the form of a bottle or bag of sufficient size to hold the customary whole blood unit (circa 450 ml.) together with an aliquot of anticoagulant. A compound may be brought into contact with the cells at any appropriate point between their collection from the donor and their transfusion (altogether with the compound) into the recipient. As one possibility therefore the compound, in association with the anticoagulant, is present within the bottle or bag when the latter is "ready for use", the admixture occurring upon entry of the blood, while in an alternative approach the compound is added to cells already held within the bottle/bag, for example immediately subsequent to collection or just prior to use (transfusion). The compounds may be used in this fashion whether the cells are stored in the form of whole blood or as a packed cell mass (when the plasma is held separately) and, in the latter case, whether transfused resuspended in plasma or in a plasma substitute.

The effective concentration of a compound, in whole blood volume in a bottle or bag as above described, will generally be in the range 0.1 mM to 50 mM, more generally in the range 0.5 mM to 25 mM and most often in the range 1 mM to 10 mM, with an optimum concentration of 3 mM. Although the precise weight of compound required will vary with its identity a standard size bottle/bag (vide supra) will require circa 0.5 g (calculated as the acid) to provide the optimum 3 mM concentration.

The compounds of formulae (II) to (IX) as hereinbefore defined may be prepared by those methods known in the art for the synthesis of compounds of analogous structure and in particular, inter alia, by methods analogous to those taught herein in respect of the compounds of formula (I) using appropriate starting materials and conditions as hereinbefore described.

It will be understood from the foregoing description that this invention may comprise any novel feature described herein, principally but not exclusively for example:

(a) Compounds of formula (I) as hereinbefore defined and salts thereof.

(b) Methods as hereinbefore described for the preparation of compounds according to (a) supra, together with the compounds when so prepared.

(c) Compounds of formula (I) as hereinbefore defined and pharmacologically acceptable salts thereof for use in the medical treatment of a mammal and in particular a human being.

(d) Compounds of formula (I) as hereinbefore defined and pharmacologically acceptable salts thereof for use in a mammal, in particular a human being, to provide a more effective delivery of oxygen to the tissues.

(e) Compounds of formula (I) as hereinbefore defined and pharmacologically acceptable salts thereof for use in a mammal, in particular a human being, in the relief of tissue hypoxia.

(f) A pharmaceutical formulation comprising a treatment-effective amount of a compound of formula (I) as hereinbefore defined or a pharmacologically acceptable salt thereof together with an acceptable carrier therefor.

(g) A method for the preparation of a formulation according to (f) supra comprising admixture of the active ingredient, as defined, with the carrier therefor.

(h) A method for providing a more effective delivery of oxygen to the tissues of a mammal, in particular a human being, comprising administering to a mammal in need thereof a non-toxic, treatment-effective amount of a compound of formula (I) as hereinbefore defined or a pharmacologically acceptable salt thereof.

(i) A method for the relief of tissue hypoxia in a mammal, in particular a human being, comprising administering to a mammal in need thereof a non-toxic, treatment-effective amount of a compound of formula (I) as hereinbefore defined or a pharmacologically acceptable salt thereof.

(j) A method for maintaining the oxygen-delivery capacity of stored mammalian red blood cells comprising admixing said cells, prior to their transfusion into a recipient mammal, with a non-toxic, maintenance-effective amount of a compound of formula (I) as hereinbefore defined or a pharmacologically acceptable salt thereof.

(k) A method for prolonging the useful storage life of stored mammalian red blood cells comprising admixing said cells, prior to their transfusion into a recipient mammal, with a non-toxic, prolongation-effective amount of a compound of formula (I) as hereinbefore defined or a pharmacologically acceptable salt thereof.

(l) A method according to (j) or (k) supra wherein the red blood cells are human in origin.

(m) A sterile, sealed vessel containing an anticoagulant and a non-toxic amount of a compound of formula (I) as hereinbefore defined or a pharmacologically acceptable salt thereof.

(n) A sterile, sealed vessel containing mammalian, in particular human, red blood cells, an effective amount of an anticoagulant and a non-toxic amount of a compound of formula (I) as hereinbefore defined or a pharmacologically acceptable salt thereof.

(o) Novel compounds of formulae (II) to (IX) as hereinbefore defined, methods for their preparation as hereinbefore described and the compounds when so prepared.

A large number of tricyclic structures have been described in the literature as active in mammals and in in vitro mammalian preparations as inhibitors of allergic reactions associated with reaginic antibodies of the kind responsible for asthma in man, see for example U.K. patent specifications Nos. 1,414,621; 1,447,031; 1,447,032; 1,452,891; 1,458,185 and 1,458,186; such compounds have thus been proposed for use in the treatment or prophylaxis of mammalian allergic conditions such as asthma and other allergic chest conditions, hay fever (allergic rhinitis), conjunctivities, urticaria and eczema.

Formula (I) as herein defined is believed to lie outside of the disclosures of all this art.

Japanese patent Kokai No. 16821/82 (laid open to public inspection on 28th January 1982) describes a drug for treating immunodeficiency diseases of mammals, e.g. man, comprising, as an effective ingredient, a compound represented by general formula:

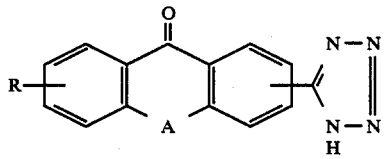

wherein R represents a hydrogen atom or a lower alkoxy group and A represents an oxygen atom or a sulfonyl group, for a salt thereof; specifically recited immunodeficiency diseases are cancer, rheumatism, autoimmune disease, hepatitis, nephritis and infectious disease.

The Japanese document identifies only three specific compounds within the general formula therein set forth, each said compound being acknowledged as previously disclosed in the literature and suggested for use in the treatment or prophylaxis of asthma and related allergic conditions. These three compounds are:

(A): 3-(1H-tetrazol-5-yl)thioxanthone-10,10-dioxide
(B): 7-methoxy-2-(1H-tetrazol-5-yl)xanthone
(C): 2-(1H-tetrazol-5-yl)xanthone.

The Japanese document thus identifies no specific compound that was not previously specifically disclosed in the literature and the subject invention is presented as the finding of a "new use" for the said "old" compounds.

None of the compounds identified in the Japanese document as (A), (B) and (C) is within formula (I) as herein defined.

The following Examples are provided in illustration of the present invention and should not be construed as in any way constituting a limitation thereof. All temperatures are in degrees Celsius.

EXAMPLE 1

7-Methoxyxanthone-3-carboxylic acid

A. 2-(4-Methoxyphenoxy)terephthalic acid

Sodium metal (11.5 g) was dissolved in methanol (250 ml) and to this solution was added 4-methoxyphenol (62.1 g). The methanol was thoroughly removed by rotary evaporation and the residual sodium salt dissolved in dimethylsulphoxide. Dimethyl 2-nitroterephthalate (107.6 g) was added and the mixture stirred and heated at 120° for 2.5 h. The dark resulting solution was hydrolysed by boiling under reflux with a solution of sodium hydroxide pellets (70 g) in water (500 ml) and ethanol (800 ml) for 2.5 h. The solution was acidified by pouring into excess iced hydrochloric acid and the precipitated 2-(4-methoxyphenoxy)terephthalic acid was filtered off, washed with water and dried at 90° in a vacuo to give 125.0 g, m.p. 280°–283°.

The following compounds were prepared similarly:

2-(4-Ethoxyphenoxy)terephthalic acid, m.p. 280°–281° from 4-ethoxyphenol prepared by the method of McElvain and Englehardt, J. Amer. Chem. Soc., (1944), 66, 1080.

2-(4-Propoxyphenoxy)terephthalic acid, m.p. 279°–281° from 4-propoxyphenol prepared by the method of Klarmann, Gatyas and Shternov, J. Amer. Chem. Soc. (1932), 54, 298.

2-(4-Isopropoxyphenoxy)terephthalic acid, m.p. 261°–263°, from acetic acid, from 4-isopropoxyphenol prepared by the method of Klarmann, Gatyas and Shternov, J. Amer. Chem. Soc. (1932), 54, 298.

2-(4-Methylthiophenoxy)terephthalic acid, m.p. 294°–296° from methanol, from 4-(methylthio)phenol.

B. 7-Methoxyxanthone-3-carboxylic acid 2-(4-Methoxyphenoxy)terephthalic acid (90.0 g) was boiled under reflux with phosphorous oxychloride (900 ml) for 2 h. The cooled reaction mixture was cautiously decomposed by adding to water, controlling the temperature at 40°–50° by ice addition. The precipitated 7-methoxyxanthone-3-carboxylic acid was filtered off, washed with water, and recrystallised from dimethylformamide (after drying at 80° in vacuo m.p. 301°–302°).

Found: C, 66.73%; H, 3.70%. $C_{15}H_{10}O_5$ requires C, 66.67%; H, 3.73%.

The following compounds were prepared similarly:

Ex.2: 7-Ethoxyxanthone-3-carboxylic acid m.p. 286°–289° (unrecrystallised).

Ex.3: 7-Propoxyxanthone-3-carboxylic acid m.p. 261°–264° from dimethylformamide.

Found: C, 68.84%; H, 4.91%. $C_{17}H_{14}O_5$ requires C, 68.46%; H, 4.70%.

Ex.4: 7-(Methylthio)xanthone-3carboxylic acid m.p. 272°–275° from acetic acid.

Found: C, 62.69%; H, 3.48%; S, 11.15%. $C_{15}H_{10}O_4S$ requires C, 62.94%; H, 3.49%; S, 11.19%.

EXAMPLE 5

7-Isopropoxyxanthone-3-carboxylic acid 2-(4-Isopropoxyphenoxy)terephthalic acid (13.5 g) was boiled under reflux with thionyl chloride (150 ml) for 0.5 h, then ferric chloride (1.0 g) was added and reflux continued for a further 4.5 h. The excess thionyl chloride was evaporated off, and the residue poured into water. The precipitated product was filtered off, washed with water, and stirred with excess aqueous sodium bicarbonate solution at 80°–90° for 1.5 h. The solution was acidified to precipitate 7-isopropoxyxanthone-3-carboxylic acid which was filtered off, washed with water and dried. It was recrystallised first from dimethylformamide, and then from acetic acid, m.p. 261°–263°.

Found: C, 68.12%; H, 4.60%. $C_{17}H_{14}O_5$ requires C, 68.46%; H, 4.70%.

EXAMPLE 6

7-Hydroxyxanthone-3-carboxylic acid

7-Methoxyxanthone-3-carboxylic acid (8.0 g) was boiled under reflux with a 12% solution of hydrogen bromide in acetic acid (500 ml) for 28 h. The reaction mixture was poured into iced water and the precipitated product filtered off, washed well with water, and dried at 100° in vacuo to yield 7-hydroxyxanthone-3-carboxylic acid m.p. 349°–350°.

Found: C, 65.59%; H, 3.14%. $C_{14}H_8O_5$ requires C, 65.63%; H, 3.12%.

EXAMPLE 7

7-Ethoxyxanthone-3-carboxylic acid (i) 7-Hydroxyxanthone-3-carboxylic acid (5.0 g) was stirred with a mixture of anhydrous potassium carbonate (50 g) and diethyl sulphate (10.25 ml; 12.0 g) in dimethylformamide (150 ml) for 5 h, then allowed to stand at room temperature for 16 h. The reaction mixture was poured into water and the residual ethyl ester of 7-ethoxyxanthone-3-carboxylic acid filtered off and hydrolysed by boiling with a solution of sodium hydroxide (2.0 g) in water (200 ml) and ethanol (50 ml) for 2 h. The cooled reaction mixture was acidified with excess hydrochloric acid, and the precipitated acid filtered off, washed with water, and recrystallised from dimethylformamide m.p. 287°–289°.

Found: C, 67.72%; H, 4.40%. $C_{16}H_{12}O_5$ requires C, 67.60%; H, 4.26%.

(ii) (A) Methyl 7-hydroxyxanthone-3-carboxylate

7-Hydroxyxanthone-3-carboxylic acid (10.0 g) was boiled under reflux with methanol (1.5 liters) and concentrated sulphuric acid (15 ml) for 3 h. The hot solution was filtered, and on cooling methyl 7-hydroxyxanthone-3-carboxylate crystallised out, and was filtered off and dried, 6.4 g, m.p. 268°–270°.

(ii) (B) 7-Ethoxyxanthone-3-carboxylic acid

Methyl 7-hydroxyxanthone-3-carboxylate (6.9 g) was boiled under reflux with stirring with ethyl iodide (9.75 g), potassium carbonate (75 g) and acetone (1 liter) for 4 h. The mixture was filtered while hot and the residue washed with acetone. The combined filtrate and washings were evaporated to dryness and the residue dissolved in dichloromethane and washed with water. The solution was dried and evaporated to give methyl 7-ethoxyxanthone-3-carboxylate, 3.65 g, m.p. 169°–171°.

The ester (3.6 g) was hydrolysed by boiling with a solution of sodium hydroxide (2.0 g) in water (250 ml) and ethanol (50 ml) for 2 h. The resulting solution was acidified with excess dilute hydrochloric acid, and the precipitated product filtered off giving 7-ethoxyxanthone-3-carboxylic acid (on recrystallisation from dimethylformamide m.p. 290°–291°).

Similarly were prepared:

Ex.8: 7-(3-Hydroxypropoxy)xanthone-3-carboxylic acid m.p. 245°–246° from acetic acid, from 3-bromo-1-propanol (methyl ester, m.p. 161°–162° from methanol).

Found: C, 65.15%; H, 4.56%. $C_{17}H_{14}O_6$ requires C, 64.97%; H, 4.49%.

Ex.9: 7-Butoxyxanthone-3-carboxylic acid m.p. 225°–227°.

Found: C, 69.09%; H, 5.16%. $C_{18}H_{16}O_5$ requires C, 69.22%; H, 5.11%.

Ex.10: 7-Propoxyxanthone-3-carboxylic acid m.p. 262°–263°, from n-propyl iodide (methyl ester, m.p. 151°–152°).

EXAMPLE 11

7-(2-Hydroxyethoxy)xanthone-3-carboxylic acid

7-Hydroxyxanthone-3-carboxylic acid (3.0 g), ethylene carbonate (13.0 g) and tetramethylammonium iodide (0.07 g) were heated together at 135° to 140° for 4 h. The cooled reaction mixture was diluted with chloroform and the solid residue filtered off and boiled with a solution of sodium hydroxide (2.0 g) in ethanol (40 ml) and water (60 ml) for 5 h. The reaction mixture was then diluted with water, filtered, and acidified with dilute hydrochloric acid, and the solid product filtered off and recrystallised from boiling dimethylformamide to yield 7-(2-hydroxyethoxy)xanthone-3-carboxylic acid m.p. 265°–267°.

Found: C, 63.43%; H, 4.11%. $C_{16}H_{12}O_6$ requires C, 64.00%; H, 4.03%.

EXAMPLE 12

7-(2-Hydroxypropoxy)xanthone-3-carboxylic acid

Methyl 7-hydroxyxanthone-3-carboxylate (2.0 g), propylene carbonate (10.0 g) and tetramethylammonium iodide (0.20 g) were heated together at 170° for 4 h. the cooled reaction mixture was then boiled under reflux with a solution of sodium hydroxide (6.0 g) in water (200 ml) and ethanol (200 ml) for 30 min. The solution was cooled, filtered, and acidified with excess dilute hydrochloric acid. The precipitated product was filtered off, washed with water, and recrystallised twice from 95% 2-butanone-5% water mixture to yield 7-(2-hydroxy-propoxy)xanthone-3-carboxylic acid m.p. 252°–254° (structure confirmed by proton magnetic resonance spectroscopy).

Found: C, 65.06%; H, 4.54%. $C_{17}H_{14}O_6$ requires C, 64.96%; H, 4.49%.

EXAMPLE 13

7-(3-Acetoxypropoxy)xanthone-3-carboxylic acid 7-(3-Hydroxypropoxy)xanthone-3-carboxylic acid (8.8 g) was boiled under reflux with acetic anhydride (200 ml) for 2 h. The resulting solution was filtered and the excess anhydride evaporated off. The residual solid was washed with water and dried, then recrystallised from acetic acid to give 7-(3-acetoxy-propoxy)xanthone-3-carboxylic acid, m.p. 236°–237°.

Found: C, 63.94%; H, 4.51%. $C_{19}H_{16}O_7$ requires C, 64.04%; H, 4.53%.

EXAMPLE 14

7-Methoxy-3-(5-Tetrazolyl)xanthone (A) 7-Methoxyxanthone-3-carboxamide.

7-Methoxyxanthone-3-carboxylic acid (20.0 g) was boiled under reflux with thionyl chloride (200 ml) for 2 h. The excess thionyl chloride was evaporated thoroughly from the solution and the residual acid chloride added to 0.880 ammonia (200 ml) with stirring. The solid 7-methoxyxanthone-3-carboxamide was filtered off, washed with water, and dried at 80° in vacuo to give 19.6 g m.p. 286°–287°.

The following amides were prepared similarly:
7-Ethoxyxanthone-3-carboxamide, m.p. 311°–314°.
7-Butoxyxanthone-3-carboxamide, m.p. 222°–225°.
7-(3-Acetoxypropoxy)xanthone-3-carboxamide, m.p. 205°–209°.
7-(2-Acetoxypropoxy)xanthone-3-carboxamide, m.p. 196°–198° from acetic acid.
7-Propoxyxanthone-3-carboxamide, m.p. 272°–274°.
7-Isopropoxyxanthone-3-carboxamide, m.p. 234°–239°.
7-(Methylthio)xanthone-3-carboxamide, m.p. 228°–234°.

(B) 6-Cyano-2-methoxyxanthone.

7-Methoxyxanthone-3-carboxamide (1.15 g) was added to a stirred solution of thionyl chloride (5.0 ml) in dimethylformamide (25 ml) at 0°–5° over about 5 minutes. The reaction mixture was stirred at 0°–5° for 1 h., then poured on to ice. The solid precipitated product was filtered off, washed with water and recrystallised from dimethylformamide, giving 6-cyano-2-methoxyxanthone, 0.60 g, m.p. 254°–255°.

The following nitriles were prepared similarly:
6-Cyano-2-ethoxyxanthone, m.p. 204°–205°, ex dimethylformamide.
2-Butoxy-6-cyanoxanthone, m.p. 156°–157° ex acetic acid.
2-(3-Acetoxypropoxy)-6-cyanoxanthone, m.p. 158°–160° ex ethanol.
2-(2-Acetoxypropoxy)-6-cyanoxanthone, m.p. 139°–140° ex methanol.
6-Cyano-2-propoxyxanthone, m.p. 166°–167° ex dimethylformamide.
6-Cyano-2-isopropoxyxanthone, m.p. 145°–146° ex aqueous dimethylformamide.
6-Cyano-2-(methylthio)xanthone, m.p. 209°–210° ex aqueous dimethylformamide.

(C) 2-Methoxy-6-(5-tetrazolyl)xanthone.

6-Cyano-2-methoxyxanthone (12.6 g) was heated with sodium azide (3.41 g) and ammonium chloride (2.95 g) in dimethylformamide (100 ml) at 125° for 6 h. The reaction mixture was diluted with water and acidified with excess hydrochloric acid. The precipitated 2-methoxy-6-(5-tetrazolyl)xanthone was filtered off, washed with water, and recrystallised from dimethylformamide, decomposes above 300°.

Found: C, 60.82%; H, 3.45%; N, 18.91%. $C_{15}H_{10}N_4O_3$ requires C, 61.22%; H, 3.42%; N, 19.04%.

Similarly were prepared:
Ex. 15: 2-Ethoxy-6-(5-tetrazolyl)xanthone.
Decomp. 272°–274° from dimethylformamide.
Found: C, 62.01%; H, 3.94%; N, 18.20%. $C_{16}H_{12}N_4O_3$ requires C, 62.33%; H, 3.92%; N, 18.17%.
Ex. 16: 2-Propoxy-6-(5-tetrazolyl)xanthone
Decomp. 272°–273° from dimethylformamide.
Found: C, 63.39%; H, 4.37%; N, 17.15%. $C_{17}H_{14}N_4O_3$ requires C, 63.35%; H, 4.38%; N, 17.38%.
Ex. 17: 2-Butoxy-6-(5-tetrazolyl)xanthone
Decomp. 249°–250° from dimethylformamide.
Found: C, 64.37%; H, 4.71%; N, 16.54%. $C_{18}H_{16}N_4O_3$ requires C, 64.28%; H, 4.79%; N, 16.66%.
Ex. 18: 2-Isopropoxy-6-(5-tetrazolyl)xanthone
Decomp. 263°–265° from 2-methoxyethanol.
Found: C, 63.27%; H, 4.37%; N, 17.25%. $C_{17}H_{14}N_4O_3$ requires C, 63.35%; H, 4.35%; N, 17.39%.

Ex. 19: 2-(Methylthio)-6-(5-tetrazolyl)xanthone
M.p. 253°–255° from aqueous 2-methoxyethanol.
Found: C, 58.34%; H, 3.23%; N, 17.97%; S, 10.29%. $C_{15}H_{10}N_4O_2S$ requires C, 58.06%; H, 3.22%; N, 18.06%; S, 10.32%.

EXAMPLE 20

2-(3-Hydroxypropoxy)-6-(5-tetrazolyl)xanthone 2-(3-Acetoxypropoxy)-6-cyanoxanthone (3.25 g), sodium azide (0.66 g), ammonium chloride (0.57 g) and dimethylformamide (50 ml) were heated together at 125° for 5 h. The reaction mixture was poured into water, and made alkaline with sodium hydroxide solution. The solution was extracted twice with chloroform to remove unchanged nitrile, and then acidified with hydrochloric acid to precipitate crude 2-(3-acetoxypropoxy)-6-(5-tetrazolyl)xanthone, 2.85 g, m.p. 240° (decomposes).

The acetoxy compound (1.5 g) was boiled under reflux with sodium hydroxide (3.0 g) in water (30 ml) for 1.5 h., and the solution acidified with hydrochloric acid. The precipitated solid was filtered off and recrystallised from dimethylformamide to yield 2-(3-hydroxypropoxy)-6-(5-tetrazolyl)xanthone m.p. 270° (decomposes).

Found: C, 60.37%; H, 4.27%; N, 16.72%. $C_{17}H_{14}N_4O_4$ requires C, 60.35%; H, 4.17%; N, 16.56%.

Similarly prepared was:
Ex. 21: 2-(2-Hydroxypropoxy)-6-(5-tetrazolyl)xanthone
M.p. 250° (decomposes).
Found: C, 60.08%; H, 4.21%; N, 16.62%. $C_{17}H_{14}N_4O_4$ requires C, 60.35%; H, 4.17%; N, 16.56%.

EXAMPLE 22

7-Methoxyxanthene-3-carboxylic acid

7-Methoxyxanthone-3-carboxylic acid (10.0 g) was reduced by the Clemmensen method, using zinc amalgam prepared from zinc powder (100 g) and mercuric chloride (8.0 g), in acetic acid at ambient temperature. The product, 7-methoxyxanthene-3-carboxylic acid, was obtained by chromatography on silica gel, eluting with 5% methanol in chloroform, and had m.p. 259°–261°.

Found: C, 70.41%; H, 4.78%. $C_{15}H_{12}O_4$ requires C, 70.30%; H, 4.72%.

Preparation of sodium salts

7-Methoxyxanthone-3-carboxylic acid sodium salt (Ex. 1a)

7-Methoxyxanthone-3-carboxylic acid (32.9 g) was heated with a solution of sodium bicarbonate (10.08 g) in water 1 liter), the solution filtered and evaporated to dryness. The residual solid was ground to a powder and dried in vacuo over calcium chloride to give the sodium salt, analysing for 0.25 mole water of crystallisation.

Found: C, 60.61%; H, 3.22%. $C_{15}H_9NaO_5.0.25 H_2O$ requires C, 60.72%; H, 3.23%.

The following sodium salts were similarly prepared from the fully characterised free carboxylic acids or tetrazoles. The number of moles of water of crystallisation may vary for different preparations of the same sodium salt, according to the conditions of drying and exposure to atmospheric moisture:

7-Ethoxyxanthone-3-carboxylic acid sodium salt (Ex. 2a)
Freeze dried, monohydrate.

Found: C, 59.43%; H, 3.52%. $C_{16}H_{11}NaO_5.H_2O$ requires C, 59.26%; H, 4.04%.

7-Propoxyxanthone-3-carboxylic acid sodium salt (Ex. 3a)

Freeze dried, monohydrate.

Found: C, 60.49%; H, 4.12%. $C_{17}H_{13}NaO_5.H_2O$ requires C, 60.35%; H, 4.47%.

7-Isopropoxyxanthone-3-carboxylic acid sodium salt (Ex. 5a)

Freeze dried, monohydrate.

Found: C, 59.72%; H, 4.00%; Loss on drying at 120°, 4.94%. $C_{17}H_{13}NaO_5.H_2O$ requires C, 60.35%; H, 4.47%; $H_2O$, 5.33%.

7-(Methylthio)xanthone-3-carboxylic acid sodium salt (Ex. 4a)

Freeze dried, monohydrate.

Found: C, 55.63%; H, 3.21%; S, 9.70%; Loss on drying at 120%, 4.78%. $C_{15}H_9NaO_4S.H_2O$ requires C, 55.20%; H, 3.40%; S, 9.82%; $H_2O$, 5.52%.

7-Hydroxyxanthone-3-carboxylic acid sodium salt (Ex. 6a)

Dried at room temperature in vacuo; dihydrate.

Found: C, 53.67%; H, 2.79%. $C_{14}H_7NaO_5.2H_2O$ requires C, 53.50%; H, 3.53%.

7-(2-Hydroxyethoxy)xanthone-3-carboxylic acid sodium salt (Ex.11a)

Dried at room temperature; sesquihydrate.

Found: C, 54.93%; H, 3.92%. $C_{16}H_{11}NaO_6.1.5H_2O$ requires C, 55.02%; H, 4.04%.

7-(3-Hydroxypropoxy)xanthone-3-carboxylic acid sodium salt (Ex. 8a)

Dried at 80° in vacuo, hemihydrate.

Found: C, 55.68%; H, 3.64%. $C_{17}H_{13}N_4NaO_4.0.5H_2O$ requires C, 55.29%; H, 3.82%.

2-Methoxy-6-(5-tetrazolyl)xanthone sodium salt (Ex. 14a)

Dried at 80° in vacuo, exposed to air at room temperature. Tetrahydrate.

Found: C, 46.44%; H, 4.34%; N, 14.58%. $C_{15}H_9N_4NaO_3.4H_2O$ requires C, 46.40%; H, 4.41%; N, 14.43%.

2-Ethoxy-6-(5-tetrazolyl)xanthone sodium salt (Ex. 15a)

Dried at 80° in vacuo, exposed to air at room temperature. Monohydrate.

Found: C, 55.34%; H, 4.00%; N, 16.11%. $C_{16}H_{11}N_4NaO_3.H_2O$ requires C, 55.17%; H, 3.76%; N, 16.08%.

2-Propoxy-6-(5-tetrazolyl)xanthone sodium salt (Ex. 16a)

Dried at room temperature, 2.25 hydrate.

Found: C, 53.15%; H, 4.36%; N, 14.65%. $C_{17}H_{14}N_4NaO_3.2.25H_2O$ requires C, 53.05%; H, 4.58%; N, 14.56%.

2-Isopropoxy-6-(5-tetrazolyl)xanthone sodium salt (Ex. 18a)

Freeze dried, 3.5 hydrate.

Found: C, 50.13%; H, 4.58%; N, 13.36%; loss on drying at 120°, 14.77%. $C_{17}H_{13}N_4NaO_3.3.5H_2O$, requires C, 50.12%; H, 4.95%; N, 13.75%; $H_2O$, 15.48%.

2-(Methylthio)-6-(5-tetrazolyl)xanthone sodium salt (Ex. 19a)

Freeze dried, trihydrate.

Found: C, 46.69%; H, 3.74%; N, 14.31%; S, 8.11%; loss on drying at 120°, 13.81%. $C_{15}H_9N_4NaO_2S.3H_2O$ requires C, 46.63%; H, 3.91%; N, 14.50%; S, 8.30%; $H_2O$, 13.99%.

2-(2-Hydroxypropoxy)-6-(5-tetrazolyl)xanthone sodium salt (Ex. 21a)

Dried at 80° in vacuo, monohydrate.

Found: C, 53.96%; H, 4.00%; N, 14.58%. $C_{17}H_{13}N_4NaO_4.H_2O$ requires C, 53.97%; H, 4.07%; N, 14.81%.

2-(3-Hydroxypropoxy)-6-(5-tetrazolyl)xanthone sodium salt (Ex. 20a)

Dried at 80° in vacuo, one-third hydrate.

Found: C, 58.68%; H, 3.64%; N, 15.14%. $C_{17}H_{13}N_4NaO_4.0.33H_2O$ requires C, 55.74%; H, 3.76%; N, 15.29%.

EXAMPLE 23

7-(2-Acetoxyethoxy)xanthone-3-carboxylic acid 7-(2-Hydroxyethoxy)xanthone-3-carboxylic acid (4.0 g) was boiled under reflux with acetic anhydride (200 ml) for 3 h. The solution was evaporated to dryness and the residue recrystallised from acetic acid to yield 7-(2-acetoxyethoxy)xanthone-3-carboxylic acid, m.p. 248°–249° C.

Found: C, 63.08%; H, 4.18%. $C_{18}H_{14}O_7$ requires C, 63.16%; H, 4.12%

EXAMPLE 24

2-(2-Acetoxyethoxy)-6-(5-tetrazolyl)xanthone (A) 7-(2-Acetoxyethoxy)xanthone-3-carboxamide 7-(2-Acetoxyethoxy)xanthone-3-carboxylic acid (3.4 g) was boiled under reflux with thionyl chloride (50 ml) for 2 h. The resulting solution was evaporated to dryness and the residual acid chloride added to ice-cold concentrated ammonia solution with stirring. After 2 h the amide was filtered off and dried, yielding 3.3 g, m.p. 230°–232° C.

(B) 2-(2-Acetoxyethoxy)-6-cyanoxanthone

The amide from step (A) (3.3 g) was added to a solution of thionyl chloride (7 ml) in dimethylformamide (50 ml) at −10° C. The mixture was stirred at ice-bath temperature for 3 h, then poured into iced water. The precipitated nitrile was filtered off, washed with water, and dried to yield 2.9 g, m.p. 194°–196° C.

(C) 2-(2-Acetoxyethoxy)-6-(5-tetrazolyl)xanthone

The cyanoxanthone from step (B) (2.9 g), sodium azide (0.61 g), ammonium chloride (0.53 g) and dimethylformamide (50 ml) were heated together at 125° for 8 h. The reaction mixture was poured into an iced aqueous solution of hydrochloric acid (excess) and the product filtered off and dried. Recrystallisation from dimethylformamide yielded the title compound, m.p. 216°–218° C.

Found: C, 58.96%; H, 3.84%; N, 15.01%. $C_{18}H_{14}N_4O_5$ requires C, 59.02%; H, 3.85%; N, 15.29%.

EXAMPLE 25

2-(2-Hydroxyethoxy)-6-(5-tetrazolyl)xanthone 2-(2-Acetoxyethoxy)-6-(5-tetrazolyl)xanthone (1.0 g) was boiled under reflux with a solution of sodium hydroxide (2.0 g) in water (20 ml) for 2.5 h. The solution was cooled and poured into excess aqueous hydrochloric acid and the precipitated product filtered off, washed with water, and dried. Recrystallisation from dimethylformamide gave the title compound, m.p. 270° C. (decomposes).

Sodium salt (Ex. 25a)

The free tetrazole (13.45 g) was dissolved by warming with a solution of sodium bicarbonate (3.48 g) in water (150 ml). The cooled solution was filtered, extracted once with chloroform, and evaporated to dryness. The residue was dried at room temperature in vacuo over phosphorus pentoxide to yield 2-(2-hydroxyethoxy)-6-(5-tetrazolyl)-xanthone sodium salt dihydrate.

Found: C, 50.46%; H, 3.79%; N, 14.52%. $C_{16}H_{15}N_4NaO_6$ requires C, 50.26%; H, 3.95%; N, 14.66%.

EXAMPLE 26

2-[2-(2-Hydroxyethoxy)ethoxy]xanthone-6-carboxylic acid

2-Hydroxyxanthone-3-carboxylic acid (75.0 g), ethylene carbonate (325 g) and tetrabutylammonium iodide (1.75 g) were heated together at 170 with stirring for 5 h. The cooled reaction mixture was diluted with ethanol and the solid residue filtered off and boiled with sodium hydroxide (175 g) in ethanol (1.0 l) and water (1.0 l) for 4 h. The mixture was filtered, and the filtrate diluted with water (2.0 l) and acidified with dilute hydrochloric acid. The solid product was filtered off, washed with water and recrystallised for 2-methoxyethanol, m.p. 188° C.

|  | Analysis | |
| --- | --- | --- |
|  | C | H |
| Calc % | 62.78 | 4.68 |
| Found % | 62.52 | 4.73 |

Ex. 26a

The above product acid (1 g) was boiled with sodium bicarbonate (0.244 g) in water (200 ml); the cooled solution was filtered and freeze dried to yield the sodium salt as a pale yellow solid, m.p. greater than 350° C.

EXAMPLE 27

2-(2-Butyryloxyethoxy)xanthone-6-carboxylic acid 2-(2-Hydroxyethoxy)xanthone-6-carboxylic acid (10 g) was refluxed with butyric anhydride (250 ml) for 2 h. The resultant solution was evaporated and the residue triturated with ether. Recrystallisation from dimethylformamide/water gave the title carboxylic acid, m.p. 237°–241° C.

|  | Analysis | |
| --- | --- | --- |
|  | C | H |
| Calc % | 64.86 | 4.89 |
| Found % | 65.05 | 4.87 |

Ex. 27(a)

The corresponding sodium salt was obtained as a pale yellow solid, m.p. greater than 350° C.

EXAMPLE 28

2-[2-(2-Acetoxyethoxy)ethoxy]xanthone-6-carboxylic acid

2-[2-(2-Hydroxyethoxy)ethoxy]xanthone-6-carboxylic acid (10 g) was refluxed in acetic anhydride (150 ml) for 2 h. The resultant solution was evaporated and the residue triturated with ether. Recrystallisation from methanol gave the product as yellow crystals, m.p. 199°–200° C.

|  | Analysis | |
| --- | --- | --- |
|  | C | H |
| Calc % | 62.17 | 4.69 |
| Found % | 62.08 | 4.63 |

Ex. 28a

The corresponding sodium salt was obtained as a pale yellow solid, m.p. greater than 350° C.

EXAMPLE 29

2-(2-Butyryloxyethoxy)-6-(5-tetrazolyl)xanthone (A) 2-(2-Butyryloxyethoxy)xanthone-6-carboxamide 2-(2-Butyryloxyethoxy)xanthone-6-carboxylic acid (8.0 g) was refluxed with thionyl chloride (100 ml) for 1 h. The resultant solution was evaporated to dryness and the residual acid chloride added portionwise to ice-cold 0.880 ammonia solution with stirring. After 2 h the solid was filtered off and washed with water. Recrystallisation from 2-methoxyethanol gave the indicated product, m.p. 205°–207° C.

|  | Analysis | | |
| --- | --- | --- | --- |
|  | C | H | N |
| Calc % | 65.03 | 5.19 | 3.79 |
| Found % | 65.35 | 5.18 | 3.67 |

(B) 2-(2-Butyryloxyethoxy)-6-cyanoxanthone

Thionyl chloride (10 ml) was added dropwise to a stirred suspension of the carboxamide from step (A) (5.22 g) in dimethylformamide (100 ml) at −10° C. The mixture was kept at ice bath temperature for 1 h, then poured into iced-water. The solid precipitate was filtered off and recrystallised from glacial acetic acid yielding the title cyanoxanthone, m.p. 145°–147° C.

(C) 2-(2-Butyryloxyethoxy)-6-(5-tetrazolyl)xanthone

The cyanoxanthone from step (B) (4.17 g), sodium azide (0.82 g) ammonium chloride (0.70 g) and dimethylformamide (100 ml) were stirred together at 120° C. for 8 h. The cooled mixture was poured into iced 2M hydrochloric acid, warmed to 50° C. for 10 minutes, cooled and filtered. The resultant solid was recrystallised from dimethylformamide/water yielding the title xanthone, m.p. 207°–209° C.

|  | Analysis | | |
| --- | --- | --- | --- |
|  | C | H | N |
| Calc % | 60.90 | 4.61 | 14.22 |
| Found % | 60.93 | 4.55 | 14.12 |

Ex. 29a

The corresponding sodium salt was obtained as a pale yellow solid, m.p. 275°–280° C. (decomp.).

EXAMPLE 30

2-(Ethylthio)xanthone-6-carboxylic acid (A) Diethyl-2-(4-ethylthiophenoxy)terephthalate Sodium metal (3.4 g) was added over 20 minutes to a stirred solution of 2-(4-methylthio)terephthalic acid (10 g) in hexamethylphosphoramide (100 ml) at 100° C. under dry nitrogen. After 2 h the mixture was cooled and treated with ethyl iodide (20 ml) with ice bath cooling to maintain the temperature below 45° C. After a further 30 minutes the mixture was poured into water and ether extracted. The organic extracts were washed with brine, dried over magnesium sulphate and evaporated. Chromatography of the residual oil over silica, eluting with chloroform/60–80 petrol (2:3, v/v) and C8 Zorbax reverse phase HPLC eluting with methanol/water (7:3, v/v) gave the product as an oil.

(B) 2-(4-Ethylthiophenoxy)terephthalic acid

The diester from step (A) (1.9 g) was boiled under reflux with a solution of sodium hydroxide (5.6 g) in water (70 ml) and ethanol (30 ml). After 2 h the mixture was cooled and diluted with water (100 ml). Acidification with concentrated hydrochloric acid yielded the product acid which was filtered off and dried, m.p. 282°–284° C.

(C) 2-(Ethylthio)xanthone-6-carboxylic acid

The terephthalic acid from step (B) (1.3 g) was boiled under reflux with phosphorus oxychloride (50 ml) for 8 h. The cooled reaction mixture was cautiously decomposed by adding to water, controlling the temperature below 80° C. by ice addition. The precipitated solid was filtered off, washed with water and recrystallised from dimethylformamide/water giving the title carboxylic acid, m.p. 234°–236° C.

|  | Analysis | |
|---|---|---|
|  | C | H |
| Calc % | 63.99 | 4.03 |
| Found % | 63.98 | 4.10 |

Ex. 30a

The corresponding sodium salt was obtained as a yellow powder, m.p. greater than 350° C.

EXAMPLE 31

2-Ethylthio-6-(5-tetrazolyl)xanthone (A) 2-(Ethylthio)xanthone-6-carboxamide 2-(Ethylthio)xanthone-6-carboxylic acid (0.65 g) was boiled under reflux with thionyl chloride (50 ml) for 1 h. The resultant solution was evaporated to dryness and the residual acid chloride added portionwise to ice-cold 0.880 ammonia solution with stirring. After 2 h the solid was filtered off and washed with water yielding the product carboxamide (0.62 g), m.p. 248°–250° C.

(B) 2-Ethylthio-6-cyanoxanthone

Thionyl chloride (1.5 ml) was added dropwise to a stirred solution of the carboxamide from step (A) (0.55 g) in dimethylformamide (20 ml) at 5° C. The mixture was kept at ice-bath temperature for 1 h, then poured into iced water. The solid precipitate was filtered off, dried and chromatographed on silica eluting with methylene chloride/60–80 petrol (1:1, v/v) giving the title cyanoxanthone (0.44 g), m.p. 159°–161° C.

(C) 2-Ethylthio-6-(5-tetrazolyl)xanthone

The cyanoxanthone from step (B) (0.42 g), sodium azide (0.102 g), ammonium chloride (0.088 g) and dimethylformamide (25 ml) were stirred together at 120° C. for 10 h. The cooled mixture was poured into iced 2M hydrochloric acid, warmed to 80° C. for 10 minutes, cooled and filtered. The resultant solid was extracted into 5% sodium bicarbonate solution and washed with ether. Acidification of the base extracts gave the title compound which was filtered off and dried, m.p. 261°–262° C.

|  | Analysis | | |
|---|---|---|---|
|  | C | H | N |
| Calc % | 59.24 | 3.73 | 17.28 |
| Found % | 59.25 | 3.76 | 17.32 |

Ex. 31a

The corresponding sodium salt was obtained as a yellow powder, m.p. 335°–336° C.

EXAMPLE 32

2-(Methylthio)xanthene-6-carboxylic acid (A) 2-Methylthio-6-hydroxymethylxanthene Borane tetrahydrofuran complex (30 ml, 1M solution in tetrahydrofuran) was added under dry nitrogen to an ice cold stirred solution of 2-(methylthio)xanthone-6-carboxylic acid (3 g) in dry tetrahydrofuran (100 ml). After 1 h the mixture was allowed to attain room temperature and stirred for 12 h. The excess borane was decomposed by addition of ice and the resultant solution extracted with ethyl acetate. The organic extracts were washed with brine, dried over magnesium sulphate and evaporated yielding the title compound (2.39 g) as a white solid, m.p. 151°–153° C.

(B) 2-(Methylthio)xanthene-6-carboxaldehyde

Under dry nitrogen, dimethylsulphoxide (5 ml) was added dropwise to a stirred solution of oxalyl chloride (0.89 ml) in methylene chloride (5 ml) at −60° C. After 2 minutes a solution of the xanthene from step (A) (2.3 g) in dimethylsulphoxide (35 ml) was introduced dropwise over 5 minutes whilst maintaining the temperature below −50° C. with cooling. After 15 minutes triethylamine (6.20 ml) was added, the mixture allowed to warm to room temperature and then poured into water. The mixture was ethyl acetate extracted, the organic layers were combined, washed with brine, dried over magnesium sulphate and evaporated yielding the title carboxaldehyde (1.97 g), m.p. 122°–123° C.

(C) 2-Methylthio-6-cyanoxanthene

A mixture of the carboxaldehyde from step (B) (1.75 g), hydroxylamine hydrochloride (0.56 g), sodium formate (1 g) and formic acid (15 ml) was refluxed for 1 h. The resultant solution was diluted with water and ether extracted, the extracts were washed with brine, dried over magnesium sulphate and evaporated. The residual solid was chromatographed over silica eluting with chloroform/methanol (98:2, v/v) yielding the title cyanoxanthene (1.58 g), m.p. 142°–144° C.

(D) 2-(Methylthio)xanthene-6-carboxylic acid

The cyanoxanthene from step (C) (0.3 g) was boiled under reflux with a solution of sodium hydroxide (3 g) in water (10 ml) and ethanol (10 ml) for 6 h. The resultant solution was diluted with water, ether extracted, and acidified with concentrated hydrochloric acid. The precipitated carboxylic acid was filtered off, washed with water and dried, m.p. 266°–267° C.

| | Analysis | |
|---|---|---|
| | C | H |
| Calc % | 66.20 | 4.45 |
| Found % | 66.24 | 4.82 |

Ex. 32a

The corresponding sodium salt was obtained as a white powder, m.p. greater than 300° C.

EXAMPLE 33

2-Hydroxy-6-(5-tetrazolyl)xanthone (A) 3-(5-Tetrazolyl)xanthone 3-(5-Tetrazolyl)thioxanthone-10,10-dioxide sodium salt (U.K. patent specification No. 1,447,031; 45.0 g) was stirred and boiled under reflux with 2-normal sodium hydroxide solution for 6½ hours. The solution was acidified by pouring into excess hydrochloric acid solution and the precipitated product filtered off and recrystallised from dimethylformamide to give the title compound (14.95 g), m.pt. 296° C. (decomposes).

Calculated: C, 63.64%, H, 3.05%, N, 21.20%. Found: C, 63.77%, H, 3.05%, N, 21.15%.

(B) 2-Nitro-6-(5-tetrazolyl)xanthone 3-(5-Tetrazolyl)xanthone (1.0 g) was dissolved in concentrated sulphuric acid (10.0 ml) and the resulting solution cooled to below 15° C. Potassium nitrate (0.50 g) was added in small portions over 10 min. with cooling to maintain the temperature between 10° and 15° C. and the reaction mixture was then stirred at 20° C. for 1 hr. The reaction mixture was poured on to ice and the precipitated product filtered off, washed with water and recrystallised from dimethylformamide. The crystallised product was washed with methanol and dried at 156° C./20 mm Hg to yield 0.78 g, mpt. ca. 280° C. with decomposition.

Found: C, 54.11%; H, 2.25%; N, 22.60% $C_{14}H_7N_5O_4$. Requires: C, 54.38%, H, 2.28%; N, 22.65%.

(C) 2-Amino-6-(5-tetrazolyl)xanthone

The nitroxanthone from step (B) (1.55 g) was dissolved in a solution of sodium bicarbonate (0.42 g) in water (150 ml) with warming. To the solution was added 10% palladium on carbon catalyst and the solution hydrogenated at room temperature and atmospheric pressure for 4 hr, during which time hydrogen uptake was measured as 440 ml. The solution was filtered and the filtrate acidified with twice-normal hydrochloric acid solution. The amino-compound was filtered from the warmed mixture, washed well with water and dried to yield 0.98 g, mpt. 296°-297° C. with decomposition.

Found: C, 56.38%; H, 3.71%; N, 23.58% $C_{14}H_9N_5O_2H_2O$. Requires: C, 56.57%; H, 3.73%; N, 23.56%.

(D) 2-Hydroxy-6-(5-tetrazolyl)xanthone

The aminoxanthone from step (C) (14.4 g) was dissolved in concentrated sulphuric acid (250 ml) and to the stirred solution at 10°-15° C. was added in portions sodium nitrite (3.6 g). The solution was then stirred at 15° C. for 1 hr, poured on to ice (2 kg) and water (2.5 l). The mixture was slowly brought to the broil and boiled under reflux for 1 hr. The resulting yellow product was filtered off, washed well with water and dried.

A sample was purified by chromatography on silica gel, eluting with chloroform-methanol 3:1 v/v, mpt.

Found: C, %; H, %; N, % $C_{14}H_8N_4O_3$. Requires: C, 60.00%; H, 2.87%; N, 20.00%.

EXAMPLE 34

2-(2-Hydroxyethylthio)-6-(5-tetrazolyl)xanthone

2-Amino-6-(5-tetrazolyl)xanthone (4.60 g) was dissolved by stirring in concentrated sulphuric acid (80 ml) at 15° C. while in portions, over 10 min, was added sodium nitrite (1.15 g) with cooling to maintain the temperature at 15° C. The mixture was stirred at 15° C. for 1 hr, then poured on to ice. The solid diazonium sulphate was filtered off and washed with a little cold water.

The solid salt was added to a hot (50° C.) solution of 2-mercaptoethanol (5 ml) in water (50 ml) in portions. Vigorous effervescence took place. The mixture was kept at 50° C. for 30 min, then the solid product was filtered off and washed with water. Flash chromatography of the dried crude product on silica gel, eluting with chloroform-acetic acid 4:1 v/v, followed by recrystallisation once from aqueous dimethylformamide and twice from 2-methoxyethanol, yielded the title compound, mpt. 249° C. (with decomposition), structure supported by n.m.r. spectroscopy.

Found: C, 56.09%; H, 3,69%; N, 16.28% $C_{16}H_{12}N_4O_5S$. Requires: C, 56.46%; H, 3.55%; N, 16.46%.

EXAMPLE 35

Activity in whole human blood in vitro

Human blood was collected from volunteer donors into CPD anticoagulant* medium in the ratio 100 ml blood: 15 ml medium; 1 ml aliquots were dispensed into 2 ml polycarbonate vials and then kept for three hours at 4° C. to allow the cells to settle out from the plasma. The samples were then held at room temperature while the test compounds, one per vial, were added according to the following procedure to provide a 6 mM concentration in whole blood volume:

A small volume of plasma was removed from each vial:sodium salts (q.v.) were dissolved therein directly while acids (q.v.) were added to warm aqueous sodium bicarbonate (300 mM, 2 drops) which was then mixed with the plasma; in either case the compound-laden plasma was then returned to the original vial, the vial capped and the contents mixed thoroughly.

For each experimental series three control vials were also prepared containing respectively:

(a) blood alone
(b) blood+hydrochloric acid (0.1M, 150 microliter)
(c) blood+aqueous sodium hydroxide (0.1M, 150 microliter).

After a total of two hours at room temperature all samples were left at 37° C. for 16 hours and the pH of each then measured at that temperature. The vials were then stored on ice and the oxygen-dissociation curve determined for each sample using a whole-blood spectrophotometer (Hem-O-Scan, Trade Name). Finally, after rewarming to 37° C., the pH of each sample was remeasured.

The right-displacement of the $P_{50}$ point (the oxygen tension at which the haemoglobin is 50% saturated with oxygen) for the oxygendissociation curve was ascertained for each sample relative to the calculated $P_{50}$ value for the appropriate sample pH. The results are given below.

*CPD anticoagulant is an aqueous solution containing the following per 100 ml

| | |
|---|---|
| Sodium citrate | 2.63 g |
| Anhydrous dextrose | 2.32 g |
| Citric acid monohydrate | 0.327 g |
| Sodium acid phosphate | 0.251 g |

| Compound | Right-displacement (mm Hg) |
|---|---|
| Ex. 1a | 13.0 |
| Ex. 2 | 16.2 |
| Ex. 3 | 13.0 |
| Ex. 4a | 15.6 |
| Ex. 5a | 9.7 |
| Ex. 6a | 5.3 |
| Ex. 8a | 25.8 |
| Ex. 9 | 6.9 |
| Ex. 11a | 25.0 |
| Ex. 12 | 23.1 |
| Ex. 13 | 19.9 |
| Ex. 14a | 18.8 |
| Ex. 15a | 27.4 |
| Ex. 16a | 23.2 |
| Ex. 17 | 14.6 |
| Ex. 18a | 12.6 |
| Ex. 19a | 9.5 |
| Ex. 20a | 23.5 |
| Ex. 21a | 28.7 |
| Ex. 22 | 17.3 |
| Ex. 23 | 19.0 |
| Ex. 24 | 20.0 |
| Ex. 25a | 32.6 |
| Ex. 26a | 25.6 |
| Ex. 27a | 25.5 |
| Ex. 28a | 26.1 |
| Ex. 29a | 22.2 |
| Ex. 30a | 20.0 |
| Ex. 31a | 16.6 |
| Ex. 32a | 16.2 |
| Ex. 34 | 17.7 |
| (A)* | 7.6 |
| (B)* | −1.6** |
| (C)* | 3.5 |

*Japanese patent Kokai no. 16821/82: (A): 3-(1H—tetrazol -5-yl)thioxanthone-10,10-dioxide (B): 7-methoxy-2-(1H—tetrazol-5-yl)xanthone (C): 2-(1H—tetrazol-5-yl)xanthone
**denotes a left-displacement

EXAMPLE 36

Cardiovascular effects in the anaesthetised rat

Male Wistar rats (240–420 g) were used, anaesthesia being induced with halothane/oxygen and maintained by α-chloralose and sodium pentobarbitone i.v. Test compounds (Exs. 15a and 25a) were given i.v. as a solution in 5% dextrose and at a dose volume of 1.0 ml/kg given over 5 sec. and flushed in with 5% dextrose solution (0.1 ml); doses were given in ascending order at 10–30 min intervals over the range 0.001–30 mg/kg.

Both compounds induced a dose-related hypotension in the dose range 3–30 mg/kg.

No significant waveform abnormalities were apparent in the electrocardiogram following either compound.

EXAMPLE 37

Toxicity Data

The compounds indicated were administered i.v. to female CD1 mice (Charles River U.K. Ltd.).

For Ex. 15a the $LD_{50}$ was found to lie between 140 mg/kg and 200 mg/kg (calculated as the free acid).

For Ex. 25a the $LD_{50}$ was found to be greater than 600 mg/kg.

EXAMPLE 38

Pharmaceutical Formulations

| (A) | CAPSULE | |
|---|---|---|
| | Compound (acid) | 625 mg |
| | Starch 1500 | 250 mg |
| | Magnesium stearate | 8 mg |
| | | 883 mg |

Mix the ingredients using a suitable mixer and fill into capsules on a capsule filling machine.

| (B) | TABLET | |
|---|---|---|
| | Compound (acid) | 625 mg |
| | Lactose | 200 mg |
| | Polyvinylpyrrolidone | 50 mg |
| | Starch | 100 mg |
| | Magnesium stearate | 10 mg |
| | | 985 mg |

Dissolve the polyvinylpyrrolidone in a suitable volume of water. Mix the compound, lactose and starch and add the polyvinylpyrrolidone solution. Add a further quantity of water if required. Pass through a suitable screen and dry. Add the magnesium stearate, mix and compress on a tabletting machine.

| (C) | SUPPOSITORY | |
|---|---|---|
| | Compound sodium salt, equivalent to acid | 1.25 g |
| | Hard fat B.P. to | 3 ml |

Melt part of the hard fat at 50° C. maximum. Add the compound to the molten base and disperse. Add the remaining hard fat to the suspension. When a smooth homogeneous suspension has been obtained pour the suspension into 3 ml moulds.

| (D) | INJECTION | |
|---|---|---|
| | Compound sodium salt, equivalent to acid | 1.25 g |
| | Mannitol B.P. | 125.0 mg |
| | Water for injections BP/Ph/Gm to | 2.5 ml |

Dissolve the compound and the mannitol in ⅔ the final quantity of water for injections. Make to volume with more water for injections. Sterilise the solution by passage through a sterilising grade filter. Fill 2.5 ml portions into suitable vials under aseptic conditions and freeze dry. When drying is complete seal the vials under an atmosphere of oxygen free nitrogen and cap with aluminium collars.

| (E) | INJECTION | |
|---|---|---|
| | Compound (acid) | 2.50 g |
| | Benzyl alcohol | 90.0 mg |
| | TRIS solution (0.05 M) | 5 ml |
| | Hydrochloric acid (0.1 N) | 3 ml |
| | Water for injections BP/Ph/Gm to | 10 ml |

Dissolve the compound in the TRIS and hydrochloric acid. Add and dissolve the benzyl alcohol and make to volume with water for injections. Sterilise the solution by filtration through a suitable sterilising grade filter. Fill into 10 ml vials under aseptic conditions and seal with rubber closures.

In the foregoing, (acid) indicates that the compound of formula (I)) is present as the free carboxyl or 5-tetrazolyl acid, as appropriate.

EXAMPLE 39

Blood Storage

A sterile, sealed bag (Fenwal, Travenol Laboratories Ltd., Thetford, Norfolk, England) suitable for collection of 420 ml blood and containing 63 ml of CPD anticoagulant solution, was taken. Under sterile conditions the anticoagulant was removed, admixed with an effective, non-toxic amount (vide supra) of a compound of formula (I) and returned to the bag and the bag then released and stored at room temperature.

Blood from a volunteer human donor was subsequently collected into the bag by conventional procedures and the full bag then stored at 4°-6° C.

What we claim is:

1. Tricyclic compounds of formula (I)

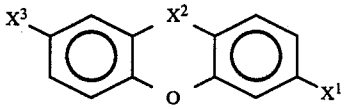

wherein
$X^1$ is a 5-tetrazolyl group
$X^2$ is a carbonyl or methylene
$X^3$ is hydroxyl or a group $—X^4(C_nH_{2n})X^5$
where
$X^4$ is oxygen or sulphur
$X^5$ is hydrogen or a group $—OX^6$
where
$X^6$ is hydrogen, alkanoyl of 1 to 4 carbon atoms or a group $—(C_mH_{2m})X^7$
where
$X^7$ is hydrogen or a group $—OX^8$
where
$X^8$ is hydrogen or alkanoyl of 1 to 4 carbon atoms and m and n are each, independently, an integer from 1 to 4, together with pharmacologically acceptable salts thereof,
provided that when $X_5$ is a group $—OX^6$ then n is always greater than 1 and $X^4$ and $X^5$ are attached to different carbon atoms
and that when $X^7$ is a group $—OX^8$ then m is always greater than 1 and no single carbon atom in the radical $—(C_mH_{2m})—$ is attached to two oxygen atoms.

2. 2-(2-Hydroxyethoxy)-6-(5-tetrazolyl)xanthone and pharmacologically acceptable salts thereof.

3. A pharmacologically acceptable salt of the xanthone according to claim 2.

4. The sodium salt of the xanthone according to claim 2.

5. 2-Ethoxy-6-(5-tetrazolyl)xanthone and pharmacologically acceptable salts thereof.

6. A pharmacologically acceptable salt of the xanthone according to claim 5.

7. The sodium salt of the xanthone according to claim 5.

8. A pharmacologically acceptable salt of a tricyclic compound of formula I:

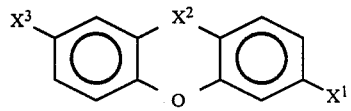

wherein
$X^1$ is a 5-tetrazolyl group
$X^2$ is carbonyl or methylene
$X^3$ is hydroxyl or a group $—X^4(C_nH_{2n})X^5$
where
$X^4$ is oxygen or sulphur
$X^5$ is hydrogen or a group $—OX^6$
where
$X^6$ is hydrogen, alkanoyl of 1 to 4 carbon atoms or a group $—(C_mH_{2m})X^7$
where
$X^7$ is hydrogen or a group $—OX^8$
where
$X^8$ is hydrogen or alkanoyl of 1 to 4 carbon atoms and m and n are each, independently, an integer from 1 to 4, provided that when $X^5$ is a group $—OX^6$ then n is always greater than 1 and $X^4$ and $X^5$ are attached to different carbon atoms and that when $X^7$ is a group $—OX^8$ then m is always greater than 1 and no single carbon atom in the radical $—(C_mH_{2-m})—$ is attached to two oxygen atoms.

9. The sodium salt of claim 8.

10. 2-(2-hydroxyethoxy)-6-(5-tetrazolyl)xanthone.

11. A pharmacologically acceptable salt of 2-(2-hydroxyethoxy)-6-(5-tetrazolyl)xanthone.

12. The sodium salt of claim 11.

13. 2-ethoxy-6-(5-tetrazolyl)xanthone.

14. A pharmacologically acceptable salt of 2-ethoxy-6-(5-tetrazolyl)xanthone.

15. The sodium salt of claim 14.

16. Tricyclic compounds of formula (I)

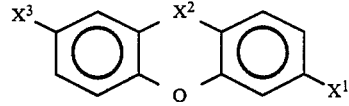

wherein
$X^1$ is a 5-tetrazolyl group
$X^2$ is a carbonyl or methylene
$X_3$ is hydroxyl or a group $—X^4(C_nH_{2n})X^5$
where
$X^4$ is oxygen or sulphur
$X^5$ is hydrogen or a group $—OX^6$
where
$X^6$ is hydrogen or alkanoyl of 1 to 4 carbon atoms and n is an integer from 1 to 4,
together with pharmacologically acceptable salts thereof,
provided that when $X^5$ is a group $—OX^6$ then n is always greater than 1 and $X^4$ and $X^5$ are attached to different carbon atoms.

17. Tricyclic compounds according to claim 16 wherein X2 is carbonyl.

18. Tricyclic compounds according to claims 17 wherein $X^3$ is a group $—X^4(C_nH_{2n})X^5$.

19. Tricyclic compounds according to claim 18 wherein $X^4$ is oxygen.

20. Tricyclic compounds according to claim 19 wherein $X^5$ is hydrogen.

21. Tricyclic compounds according to claim 19 wherein $X^5$ is a group $—OX^6$ where $X^6$ is hydrogen.

22. Tricyclic compounds according to claim 19 wherein n is 2 or 3.

23. A pharmacologically acceptable salt of a compound according to claim 16.

24. The sodium salt of a compound according to claim 16.

25. A pharmaceutical formulation comprising a compound according to any of claims 1, 2 and 5 or a pharmacologically acceptable salt thereof, together with an acceptable carrier therefor.

26. A formulation according to claim 25 in a form suitable for oral administration.

27. A formulation according to claim 25 in a form suitable for parenteral administration.

28. A formulation according to claim 25 in a form suitable for rectal administration.

* * * * *